(12) United States Patent
Koopman et al.

(10) Patent No.: US 7,750,013 B2
(45) Date of Patent: Jul. 6, 2010

(54) N-OXIDES AS PRODRUGS OF PIPERAZINE AND PIPERIDINE DERIVATIVES

(75) Inventors: Theodorus S. M. Koopman, Weesp (NL); Hendrink J. Koster, Weesp (NL); Peter H. Van Amsterdam, Weesp (NL); Roelof W. Feenstra, Weesp (NL); Marinus Verhage, Weesp (NL); Andrew C. McCreary, Weesp (NL); Mayke B. Hesselink, Weesp (NL); Gustaaf J. M. Van Scharrenburg, Weesp (NL)

(73) Assignee: Solvay Pharmaceuticals, B.V., Weesp (NL)

( * ) Notice: Subject to any disclaimer, the term of this patent is extended or adjusted under 35 U.S.C. 154(b) by 218 days.

(21) Appl. No.: 11/504,050

(22) Filed: Aug. 15, 2006

(65) Prior Publication Data
US 2007/0043059 A1   Feb. 22, 2007

Related U.S. Application Data

(60) Provisional application No. 60/709,821, filed on Aug. 22, 2005.

(51) Int. Cl.
*C07D 263/58* (2006.01)
*A61K 31/423* (2006.01)
*A61K 31/496* (2006.01)

(52) U.S. Cl. .................. 514/254.02; 544/368
(58) Field of Classification Search ........... None
See application file for complete search history.

(56) References Cited

U.S. PATENT DOCUMENTS

| 4,108,982 | A | 8/1978 | Amschler | |
|---|---|---|---|---|
| 6,878,724 | B2 * | 4/2005 | Meerpoel et al. | 514/317 |
| 2006/0122190 | A1 * | 6/2006 | Feenstra et al. | 514/254.02 |

FOREIGN PATENT DOCUMENTS

| DE | 26 38 184 | 3/1977 |
|---|---|---|
| EP | 1 467 991 A0 | 10/2004 |
| WO | WO 97/36893 | 10/1997 |
| WO | WO 00/29397 | 5/2000 |
| WO | WO 01/85725 A1 | 11/2001 |

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Robichaud et al. in Annualr Reports in Medicinal Chemistry, vol. 35, p. 11-20 (2000).*
TenBrink et al.. in Annual Reports in Medicinal Chemistry, vol. 29, p. 43-51 (1994).*
Perrone et al. J. Med. Chem. vol. 42, p. 490-496 (1999).*
International Search Report dated Nov. 16, 2006, issued in International Application No. PCT/EP2006/065477.

* cited by examiner

*Primary Examiner*—Emily Bernhardt
(74) *Attorney, Agent, or Firm*—Finnegan, Henderson, Farabow, Garrett & Dunner, L.L.P.

(57) ABSTRACT

The present disclosure relates to N-oxides of certain piperazine and piperidine derivatives and to methods for the preparation of these compounds. The disclosure also relates to the use of the compounds for the manufacture of a medicament giving a beneficial effect. The disclosure also relates to the use of the compounds for the manufacture of a medicament for treating a disease or condition. The disclosure further relates to the treatment of CNS-disorders, in particular the treatment of anxiety disorders, including generalized anxiety disorder and panic disorder, obsessive compulsive disorder, aggression, addiction (including craving), depression, autism, vertigo, schizophrenia and other psychotic disorders, Parkinson's disease and disturbances of cognition and memory. The compounds have the general formula (1)

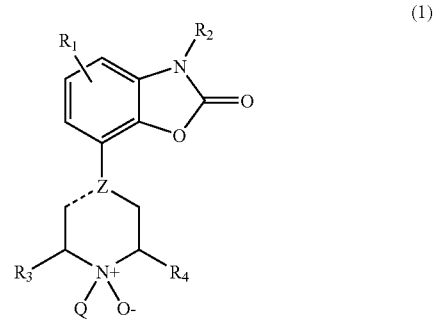

(1)

wherein the symbols have the meanings given in the specification.

8 Claims, No Drawings

N-OXIDES AS PRODRUGS OF PIPERAZINE AND PIPERIDINE DERIVATIVES

This application claims the benefit of priority of U.S. Provisional Application No. 60/709,821, filed on Aug. 22, 2005, the disclosure of which is incorporated herein by reference.

The present invention relates to N-oxides of certain piperazine and piperidine derivatives and to methods for the preparation of these compounds. The invention also relates to the use of compounds disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of CNS-disorders, in particular the treatment of anxiety disorders, including generalized anxiety disorder and panic disorder, obsessive compulsive disorder, aggression, addiction (including craving and relapse), depression, autism, vertigo, schizophrenia and other psychotic disorders, Parkinson's disease and other movement disorders and disturbances of cognition and memory.

Psychotropic Piperazine & Piperidine Derivatives

Psychotropic piperazine and piperidine derivatives are for instance known from WO 97/036893, WO 00/029397 and WO 01/085725. There are striking structural resemblances between bifeprunox, SLV308 and SLV318, the protagonists of these three patent applications. Equally striking however, are the differences between their pharmacological properties, and hence their therapeutic possibilities. Bifeprunox is a dopamine-$D_2$ receptor partial agonist and a full serotonin 5-$HT_{1A}$ receptor agonist, in clinical trials as an atypical antipsychotic agent (see R. Feenstra et al., *Bioorganic & Medicinal Chemistry Letters*, 11, 2345-2349, 2001). SLV318 is a full dopamine-$D_2$ receptor agonist and a partial serotonin 5-$HT_{1A}$ receptor agonist which potential as antidepressant and anxiolytic is currently evaluated. SLV308 is a partial dopamine-$D_2$ receptor agonist and simultaneously a full serotonin 5-$HT_{1A}$ receptor agonist. It is in clinical trials for the treatment for Parkinson's disease (see R. Feenstra et al., *Drugs of the future*, 26(2), 128-132, 2001).

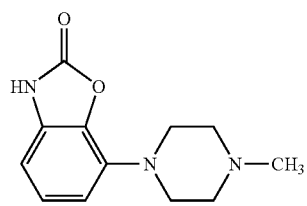

SLV308

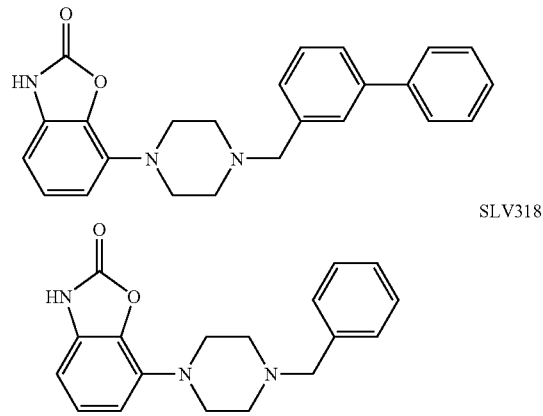

Bifeprunox

SLV318

Metabolism studies in rats, monkeys and, later, in man, revealed that SLV308 is metabolised mainly via oxidation followed by glucuronidation. But also its N-desmethyl analog and its N-oxide were detected in the plasma of all three species, after oral administration of SLV308. In man, the N-oxide accounts for approximately 30% of the administered dose.

In drug development, metabolites are routinely investigated for activity, toxicity, etc. After it was demonstrated that the N-oxide of SLV308 was a metabolite in man, the compound was synthesized and screened. It appeared virtually inactive in vitro: its affinity for the receptors for which the parent compound showed a high affinity was either very low, or below the detection limit. These findings confirmed that in this case one of the most common situations with an N-oxide had occurred: metabolic deactivation. The first in vivo experiments, in which the N-oxide was administered intravenously, seemed to substantiate the in vitro findings: the N-oxide appeared to have only approximately one tenth of the activity of the parent compound. The surprise came when the N-oxide was tested after oral administration: it then appeared to be equipotent with SLV308.

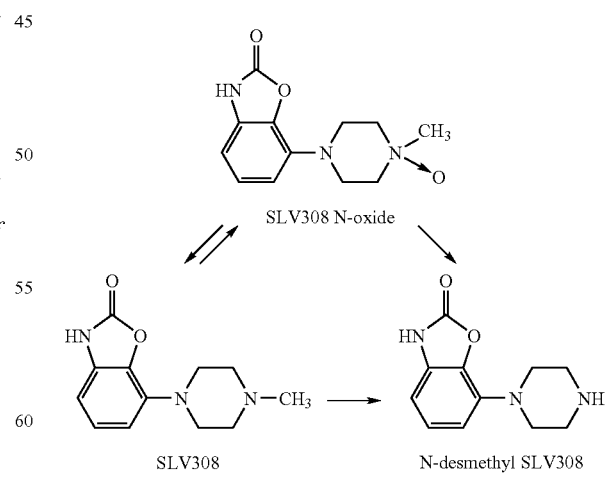

N-Oxides

N-oxides have been known since 1894. By now it is very well known that N-oxides are metabolites of many tertiary amines, and in most cases are also intermediates between tertiary amines and their N-dealkylated analogs. Most, but not all, tertiary amine drugs give rise to N-oxides. This is for instance the case with morphine, imipramine, promazine, cinnarizine and nicotine, to name just a few. The extent to what N-oxidation takes place varies from trace amounts to a near quantitative conversion. Some N-oxides were shown to be more potent than their corresponding tertiary amines. The most famous example of these is chlordiazepoxide (Librium®), one of the most frequently used drugs in psychiatric and general medicine. In many more cases however, N-oxides were found to be less potent than their corresponding tertiary amines, and N-oxidation is most commonly regarded to be metabolic deactivation. Whilst N-oxides are easily reduced to their corresponding tertiary amines by chemical means, in the human body this happens to varying degrees. Some N-oxides undergo nearly quantitative reductive conversion to the corresponding tertiary amines, in other cases the conversion is a mere trace reaction or even completely absent. (M. H. Bickel: "*The pharmacology and Biochemistry of N-oxides*", *Pharmacological Reviews,* 21(4), 325-355, 1969).

The bottom line regarding N-oxides and their corresponding tertiary amines is that everything is possible, and they are therefore unpredictable: there are examples of all kinds of extremes, and anything in between. Tertiary amines may or may not give rise to N-oxide metabolites. When they do, the N-oxidation may be a trace reaction or a quantitative conversion. N-oxides may be more active than their corresponding tertiary amines, less active or even completely inactive. N-oxides may be reduced to the corresponding tertiary amines or not. When they are, the reaction may be a mere trace or nearly quantitative.

The N-Oxide of SLV308

The combination of the facts that the N-oxide of SLV308 is inactive in vitro, moderately active in vivo when given intravenously, and virtually equipotent in vivo when given orally, can only be explained in one way. Therefore, the finding that after oral dosing of rats with the N-oxide of SLV308, plasma levels of the N-oxide and the parent compound were approximately equal, was no surprise.

The N-Oxides of Bifeprunox and SLV318

In man, neither bifeprunox nor SLV318 are metabolized to their respective N-oxides. Or, more precisely, these N-oxides were never detected in significant concentrations in blood plasma of man after administration of bifeprunox or SLV318. For this reason there never has been an incentive to synthesize and study these compounds until the unexpected findings with the N-oxide of SLV308.

The N-oxides of bifeprunox and SLV318 were synthesized and administered to mice, both intravenously and orally. It was discovered, especially after oral dosing, that both compounds proved to be prototypical prodrugs.

Of Mice and Man

As is the case in man, SLV318, when given to mice, either intravenously or orally, does not give rise to a significant amount of N-oxide as metabolite. With SLV308 the situation is different: in man the N-oxide is a major metabolite, but in mice this conversion apparently does not occur. The opposite is the case with bifeprunox: in mice the compound is significantly oxidized to the N-oxide, whilst in man this route seems to be irrelevant.

Pharmacodynamics

Since Paracelsus ('Sola dosis facit venenum') it is generally accepted that therapeutic as well as toxic effects of drugs are related to their concentration at the relevant target sites. Because generally speaking the latter are not easily accessible, blood plasma levels are used as approximations of relevant drug concentrations. During drug development plasma concentrations become known that are the lower limit for efficacy, and also concentrations at which side effects start to become apparent. In ideal situations the two concentrations are so far apart that it is easy to administer the drug in such a way that it is effective, yet does not give rise to side effects. In reality, situations are hardly ever ideal, and most drugs show side effects. In most cases the occurrence of side effects can be linked to peak plasma concentrations exceeding the lower level associated with the occurrence of side effects.

The chance finding that N-oxide metabolites of certain piperazine and piperidine derivatives, inactive by themselves, are nearly quantitatively converted into the corresponding tertiary amine compounds when given orally, created the opportunity to use them as 'prodrugs', offering the clinical benefits of an extended duration of action and a blunted peak plasma concentration, leading to an enhanced side-effect profile.

The present invention relates to compounds of the general formula (1):

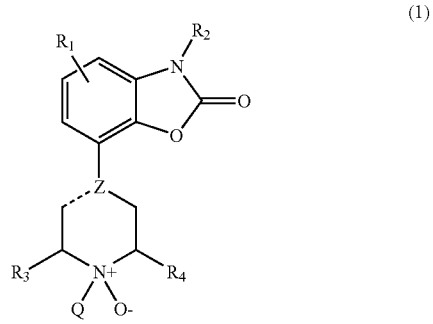

(1)

wherein:
- $R_1$ is hydrogen, halogen, alkyl($C_{1-3}$), CN, $CF_3$, $OCF_3$, $SCF_3$, alkoxy($C_{1-3}$), amino or mono- or di alkyl($C_{1-3}$) substituted amino, or hydroxy,
- - - - Z represents =C or —N,
- $R_2$ is hydrogen or alkyl($C_{1-3}$),
- $R_3$ and $R_4$ independently represent H or alkyl($C_{1-3}$), or $R_3$ and $R_4$ together can form a bridge of 2 or 3 C-atoms,
- Q is methyl, ethyl or cyclopropylmethyl which ethyl or cyclopropylmethyl groups are optionally substituted with one or more fluorine atoms, or Q is benzyl or 2-, 3- or 4-pyridylmethyl, which groups are optionally substituted with one or more substituents from the group halogen, nitro, cyano, amino, mono- or dialkyl($C_{1-3}$)amino, alkoxy($C_{1-3}$), $CF_3$, $OCF_3$, $SCF_3$, alkyl($C_{1-3}$), alkyl($C_{1-3}$)sulfonyl or hydroxyl, or Q is a group of the formula:

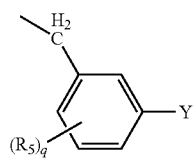

wherein:
- $R_5$ is halogen, hydroxy, alkoxy($C_{1-3}$) or alkyl($C_{1-3}$), and q is 0, 1, 2 or 3

Y is phenyl, furanyl or thienyl, which groups may be substituted with 1-3 substituents of the group hydroxy, halogen, alkoxy($C_3$), alkyl($C_{1-3}$), cyano, aminocarbonyl, mono- or dialkyl($C_{1-3}$)aminocarbonyl, and tautomers, stereoisomers, pharmacologically acceptable salts, hydrates and solvates thereof.

The invention relates to racemates, mixtures of diastereomers and the individual stereoisomers of the compounds having formula (1), as well as to and hydrates and solvates thereof. 'Alkyl($C_{1-3}$)' means 'methyl, ethyl, n-propyl or iso-propyl'.

Preferred compounds according to the invention are compounds of the formula (1) wherein $R_1$, $R_2$, $R_3$ and $R_4$ are hydrogen, and '- - - Z' and Q have the above meanings, and tautomers, stereoisomers, pharmacologically acceptable salts, hydrates and solvates thereof.

Especially preferred are the compounds wherein $R_1$, $R_2$, $R_3$ and $R_4$ are hydrogen, and '- - - Z' represents —N and Q is methyl, ethyl, benzyl or (1,1'-biphenyl)-3-yl-methyl, and tautomers, stereoisomers, pharmacologically acceptable salts, hydrates and solvates thereof.

Most preferred are the compounds wherein Q is methyl, benzyl or (1,1'-biphenyl)-3-yl-methyl, the N-oxides of SLV308, SLV318 and bifeprunox respectively, thus represented by the formulae (2-4):

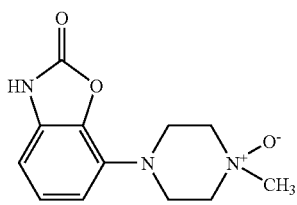

(2)

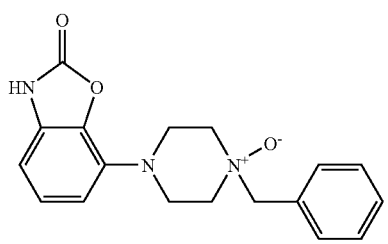

(3)

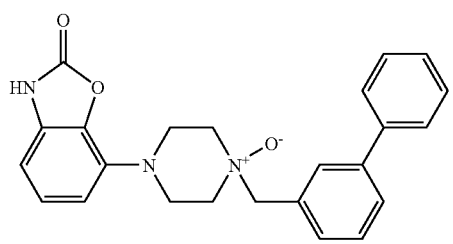

(4)

General Aspects of Syntheses

The synthesis of compounds having formula (I) is outlined in Scheme 1:

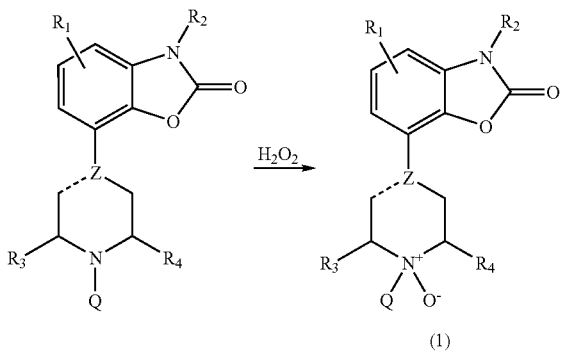

(1)

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid or an organic acid. Preferred salts of the compounds of the invention are mesylates.

Pharmaceutical Preparations

The present invention relates to pharmaceutical compositions containing N-oxides of certain piperazine and piperidine derivatives, or pharmaceutically acceptable salts thereof, as active ingredients.

For clinical use, the compounds of the invention are formulated into a pharmaceutical formulation for oral, intravenous, subcutaneous, tracheal, bronchial, intranasal, pulmonary, transdermal, buccal, rectal, parenteral or some other mode of administration. The pharmaceutical formulation contains compounds of the invention in admixture with a pharmaceutically acceptable adjuvant, diluent and/or carrier.

The total amount of active ingredients suitably is in the range of from about 0.1% (w/w) to about 95% (w/w) of the formulation, suitably from 0.5% to 50% (w/w) and preferably from 1% to 25% (w/w).

In the preparation of the pharmaceutical formulations of the present invention the active ingredients may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or pressed into tablets.

The active ingredients may be separately premixed with the other non-active ingredients, before being mixed to form a formulation. The active ingredients may also be mixed with each other, before being mixed with the non-active ingredients to form a formulation.

Soft gelatine capsules may be prepared with capsules containing a mixture of the active ingredients of the invention, vegetable oil, fat, or other suitable vehicle for soft gelatine capsules. Hard gelatine capsules may contain granules of the active ingredients. Hard gelatine capsules may also contain the active ingredients in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations may be prepared in the form of syrups or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder to be reconstituted with a suitable solvent prior to use.

Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation to by reconstituted with a suitable solvent before use.

The dose of the compound to be administered will depend on the relevant indication, the age, weight and sex of the patient and may be determined by a physician. The dosage will preferably be in the range of from 0.01 mg/kg to 10 mg/kg. The typical daily dose of the active ingredients varies within a wide range and will depend on various factors such as the relevant indication, the route of administration, the age, weight and sex of the patient and may be determined by a physician. In general, oral and parenteral dosages will be in the range of 0.1 to 1,000 mg per day of total active ingredients.

Medical and Pharmaceutical Use

Also provided according to the present invention are formulations and kits of parts for use in medical therapy; the use of formulations of the present invention in the manufacture of medicaments for use in the treatment of CNS disorders, and methods of medical treatment or comprising the administration of a therapeutically effective total amount of compounds of the invention to a patient suffering from, or susceptible to, a CNS disorder.

The term 'medical therapy' as used herein is intended to include diagnostic and therapeutic regimens carried out in vivo or ex vivo on humans or other mammals.

The formulations of the invention contain compounds of the general formula (1) either as such or, in the case of prodrugs, after administration. The formulations of the invention are thus expected to be useful in the treatment of CNS disorders.

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. The invention also includes the preparation or manufacture of said pharmaceutical compositions.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In Vitro Affinity for Neurotransmitter Receptors

The binding data collected in the table below (Example 5: pharmacological test results) were either obtained by CEREP (128, rue Danton, 92500 Rueil-Malmaison, France) or at Solvay Pharmaceuticals B.V. (C. J. van Houtenlaan 36, 1381 CP Weesp, The Netherlands), using well documented standard procedures. The affinities for dopamine-$D_2$ and 5-$HT_{1A}$ receptors for instance, was measured as described by Creese I, Schneider R and Snyder S H, [$^3$H]-Spiroperidol labels dopamine receptors in rat pituitary and brain, *Eur J Pharmacol* 1997, 46: 377-381 and Gozlan H, El Mestikawy S, Pichat L, Glowinsky J and Hamon M, 1983, Identification of presynaptic serotonin autoreceptors using a new ligand $^3$H-PAT, *Nature* 1983, 305: 140-142.

In Vitro (Ant)Agonistic Activity at Neurotransmitter Receptors

In vitro (ant)agonistic activity at different neurotransmitter receptors was for instance measured on the formation of adenylate cyclase in cell-lines expressing these cloned receptors (e.g. human $D_2$ receptors and 5-$HT_{1A}$ receptors expressed in CHO cell line according to the methods described by Solomon Y, Landos C, Rodbell M, 1974, A highly selective adenylyl cyclase assay, *Anal Biochem* 1974, 58: 541-548 and Weiss S, Sebben M and Bockaert J J, 1985, Corticotropin-peptide regulation of intracellular cyclic AMP production in cortical neurons in primary culture, *J Neurochem* 1985, 45:869-874).

In Vivo Animal Model for Serotonin 5-$HT_{1A}$ Receptor (Ant) Agonistic Activity Lower lip retraction was measured according to the method described by Berendsen et al. (Pharmacol. Biochem. Behav. 33, (1989), 821-827).

In Vivo Animal Model for Dopamine-$D_2$ Receptor (Ant)Agonistic Activity

Apomorphine-induced climbing behaviour in mice (Costall B, Naylor R J and Nohria V, Differential actions of typical and atypical agents on two behavioural effects of apomorphine in the mouse, *Brit J Pharmacol* 1978, 63: 381-382).

In Vivo Animal Models Predictive of Anxiolytic/Antidepressant Activity

The conditioned ultrasonic vocalization model in rats (Molewijk H E, Van der Poel A M, Mos J, Van der Heyden J A M and Olivier B (1995), Conditioned ultrasonic vocalizations in adult male rats as a paradigm for screening anti-panic drugs, *Psychopharmacology* 1995, 117: 32-40).

The forced swim test in rats (Porsolt R D, Anton G, Blavet N and Jalfre M, 1978, Behavioural despair in rats: A new model sensitive to antidepressant treatments, *Eur J Pharmacol* 1978, 47:379-391).

The differential reinforcement of low rates of responding model in rats (McGuire P S and Seiden L S, The effects of tricyclic antidepressants on performance under a differential-reinforcement-of-low-rate schedule in rats, *J Pharmacol Exp Ther* 1980, 214: 635-641; and van Hest et al., differential reinforcement of low rate responses, *Psychopharmacology*, 1992,107:474-479).

Suppression of locomotor activity (File S E and Hyde J R G, A test of anxiety that distinguishes between the actions of benzodiazepines and those of other minor tranquillisers or stimulants, *Pharmacol Biochem Behav* 1979, 11: 65-79).

In Vivo Animal Model Predictive of Antipsychotic Activity

Inhibition of conditioned avoidance response in rats (Van der Heyden J A M, Bradford L D, A rapidly acquired one-way conditioned avoidance procedure in rats as a primary screening test for antipsychotics: influence of shock intensity on avoidance performance, *Behav Brain Res* 1988, 31: 61-67).

In Vivo Animal Models Predictive of Anti-Parkinsonian Activity

The MPTP-lesioned Marmoset monkey (Nomoto M, Jenner P, Marsden C D: The dopamine agonist $D_2$ agonist LY 141865 but not the $D_1$ agonist SKF 38393, reverses Parkinsonism induced by 1-methyl-4-phenyl-1,2,3,6-tetrahydropyridine (MPTP) in the common Marmoset. *Neurosci. Lett.*, (1985) 57: 37-41).

6-OH-dopamine induced turning behavior in rats (Ungerstedt U, 6-OH-DA induced degeneration of central monoamine neurons, *Eur. J. Pharmacol.* 1968 5: 107-110). Specifically:

Animals

Male rats (Wistar, Harlan, Netherlands; 400-500 g at time of experiment) are housed in a temperature (20-21±2° C.) and humidity controlled environment and receive water ad libitum except during experimental sessions. Food is restricted to approximately 15 g per rat per day. A 12-hour light-dark cycle (lights on 07.00-19.00 hour) is used. All experimental procedures are conducted in accordance with Dutch law and conform to local animal care and use committee stipulations.

Surgery

Unilateral 6-hydroxydopamine (6-OHDA) lesions of the substantia nigra zona compacta are performed using a stereotaxic procedure. One hour prior to surgery, desmethylimipramine (20 mg/kg, i.p.) is administered to protect noradrenergic neurons. Rats are anaesthetized with a 3% halothane+0.8 l/min $N_2O$+0.8 l/min $O_2$-gas mixture at 1013 mbar. During surgery the gas mixture is adjusted to 1.75-2% halothane, 0.6 l/min $N_2O$ and 0.6 l/min $O_2$. The incisor bar of the stereotaxic instrument (Kopf, Calif., USA) is set at −3.3 mm, a burr hole was drilled over the substantia nigra pars compacta and 3 μl of a 6-OHDA solution (3.33 mg/ml) is injected (flow rate=0.75 μl/min; the needle is left in place for 4 minutes prior to withdrawal). Coordinates for this procedure are: anterior posterior +3.2 mm from the interaural line; medial/lateral +1.8 mm from the midline and ventral −8.2 from the skull surface. Animals are allowed to recover for approximately 2 weeks prior to testing. Good turning rats are defined as those which elicited at least 20 contralateral turns following amphetamine (2.5 mg/kg sc) in the 5 min time epoch beginning 25 min after administration and a mean of at least 20 contralateral turns recorded over a 30 min period after administration of apomorphine (0.25 mg/kg s.c.). Regular testing with apomorphine (0.1 or 0.25 mg/kg s.c.) is carried out to ensure the reliability of the animals in this procedure.

Apparatus

Eight commercially available (TSE systems Bad Homburg, Germany) 'rotameter' units (transparent plastic bowls; 57×55×52 cm) are used for testing. The rats are harnessed and tethered to a rotation sensor interfaced to an IBM compatible personal computer (using the TSE Rotameter Software v. 1.11, TSE systems Bad Homburg, Germany) which registers clockwise or counterclockwise movement. An internal software rotation filter of 10 is used.

Protocol

Following statistical randomization of the treatment groups rats are pretreated with compounds of the invention (0.1-3 mg/kg p.o.) or vehicle (2 ml/kg) and placed in the rotameters the contralateral rotational behaviour is then measured. In further studies the effects of L-DOPA (1-10 mg/kg p.o.) are assessed on contralateral rotations. The peripheral decarboxylase inhibitor benserazide (30 mg/kg i.p.) can be used. In combination studies a range of L-DOPA (1-10) doses and doses of compounds of the invention (0.1-3 mg/kg p.o.) can be combined.

The compounds of the invention of the general formula (1), as well as the pharmacologically acceptable salts thereof, are prodrugs of compounds having dopamine-$D_2$ receptor (partial) agonistic activity combined with 5-$HT_{1A}$ receptor agonistic activity. They are useful in the treatment of CNS disorders, in particular anxiety disorders, including generalized anxiety disorder and panic disorder, obsessive compulsive disorder, aggression, addiction (including craving and relapse), depression, autism, vertigo, schizophrenia and other psychotic disorders, Parkinson's disease and other movement disorders and disturbances of cognition and memory.

Treatment

The term "treatment" as used herein refers to any treatment of a mammalian, preferably human condition or disease, and includes: (1) inhibiting the disease or condition, i.e., arresting its development, (2) relieving the disease or condition, i.e., causing regression of the condition, or (3) relieving the conditions caused by the disease, i.e., stopping the symptoms of the disease.

Abbreviations

In this applications some abbreviations are used that may not be completely unambiguous for the person skilled in the art. Those are:

6-OH-DA=6-hydroxydopamine bifeprunox=7-[4-([1,1'-biphenyl]-3-ylmethyl)-1-piperazinyl]-2(3H)-benzoxazolone CHO=Chinese hamster ovary CNS=central nervous system i.p.=intraperitoneally i.v.=intravenously MPTP=1-methyl-4-phenyl-1,2,3,6-tetrahydropyridine p.o.=(per os)=orally SLV308=7-[(4-methyl)-1-piperazinyl]-2(3H)-benzoxazolone SLV318=7-[(4-methylphenyl)-1-piperazinyl]-2(3H)-benzoxazolone

EXAMPLES

The specific compounds of which the synthesis is described below are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

Example 1

Materials and Methods

Flash chromatography refers to purification using the indicated eluent and silica gel (either Acros: 0.030-0.075 mm or Merck silica gel 60: 0.040-0.063 mm).

Melting points were recorded on a Büchi B-545 melting point apparatus.

Liquid Chromatography-Mass Spectrometry (LC-MS)

The LC-MS system consists of 2 Perkin elmer series 200 micro pumps. The pumps are connected to each other by a 50 µl tee mixer, connected to a Gilson 215 auto sampler. The method is as follows:

| step | total time | flow (ul/min) | A (%) | B (%) |
|---|---|---|---|---|
| 0 | 0 | 2000 | 95 | 5 |
| 1 | 1.8 | 2000 | 0 | 100 |
| 2 | 2.5 | 2000 | 0 | 100 |
| 3 | 2.7 | 2000 | 95 | 5 |
| 4 | 3.0 | 2000 | 95 | 5 |

A = 100% Water with 0.025% HCOOH and 10 mmol NH4HCOO pH = +/−3
B = 100% ACN with 0.025% HCOOH The auto sampler has a 2 µl injection loop. The auto sampler is connected to a Waters Atlantis C18 30*4.6 mm column with 3 µm particles. The column is thermo stated in a Perkin Elmer series 200 column oven at 40° C. The column is connected to a Perkin Elmer series 200 UV meter with a 2.7 µl flowcel. The wavelength is set to 254 nm. The UV meter is connected to a Sciex API 150EX mass spectrometer. The mass spectrometer has the following parameters: Scanrange: 150-900 a.m.u.; polarity: positive; scan mode: profile; resolution Q1: UNIT; step size: 0.10 a.m.u.; time per scan: 0.500 sec; NEB: 10; CUR: 10; IS: 5200; TEM: 325; DF: 30; FP: 225 and EP: 10. The light scattering detector is connected to the Sciex API 150. The light scattering detector is a Sedere Sedex 55 operating at 50° C. and 3 bar $N_2$. The complete system is controlled by a G3 powermac.

All reactions involving moisture sensitive compounds or conditions were carried out under an anhydrous nitrogen atmosphere. Reactions were monitored by using thin-layer chromatography (TLC) on silica coated plastic sheets (Merck precoated silica gel 60 F254) with the indicated eluent. Spots were visualised by UV light (254 nm) or iodine ($I_2$). Dichloromethane (phosphorous pentoxide and calciumhydride), tetra-hydrofuran (sodium/benzophenone ketyl) and light petroleum (60-80) were distilled freshly prior to use. All other commercially available chemicals were used without further purification.

Example 2

Syntheses of Intermediates

The N-oxides of the invention were synthesized from the corresponding tertiary amines, compounds which syntheses were described in WO 97/036893, WO 00/029397 and WO 01/085725.

Example 3

Syntheses of Specific Compounds

The specific compounds of which the synthesis is described below are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

Compound 1: N-Oxide of SLV308

A suspension of 1.17 g (5.00 mmol) 7-[(4-methyl)-1-piperazinyl]-2(3H)-benz-oxazolone in 30 ml absolute ethanol is heated until a clear solution is obtained. To the hot solution is then added 0.41 ml 30% $H_2O_2$ in one portion after which the mixture is heated to reflux on an oil bath. After 5 hours reflux another portion of 0.41 ml 30% $H_2O_2$ is added and refluxing is continued for 16 hours. A small amount of 10% Pd/C is then added and after 45 minutes refluxing the reaction mixture is allowed to cool down to room temperature to give a brown suspension. The suspension is concentrating using a rotary evaporater to a brown solid which is purified by flash chromatography on silica gel (230-400 mesh, eluent DCM:MeOH:$NH_3$ 68:30:2) to obtain 1.06 g (4.25 mmol, 85% yield) of the corresponding N-oxide, compound 1 (mp 242-243° C.). Using $^1$H-NMR spectroscopy, the purity of Compound 1 was determined to be greater than 97%.

Compound 2: N-Oxide of SLV318

To a solution of 1.5 g (4.85 mmol) SLV318 (7-[(4-methylphenyl)-1-piperazinyl]-2(3H)-benzoxazolone) in 150 ml acetone, 1.26 g (5.14 mmol) 70% m-chloroperbenzoicacid is added, and the mixture is stirred for one hour and evaporated on silica. The SLV318 N-oxide (compound 2) is isolated by flash chromatography (DCM:MeOH:$NH_3$ 84:15:1). Yield 1.48 g (94%). M.p. 238-240° C. Using $^1$H-NMR spectroscopy, the purity of Compound 2 was determined to be greater than 96%.

Compound 3: N-Oxide of Bifeprunox 30 g (66 mmol) bifeprunox (7-[4-([1,1'-biphenyl]-3-ylmethyl)-1-piperazinyl]-2(3H)-benzoxazolone) is dissolved in 500 ml acetonitrile and 130 ml water. Next, 20 ml 35% $H_2O_2$ is added and the mixture is stirred at 50° C. More $H_2O_2$ is added after 2 hours (100 ml), 24 hours (100 ml) and 48 hours (100 ml). After 120 hours part of the acetonitrile is evaporated and 3000 ml water is added. The product is isolated by extraction with DCM and evaporation. The N-oxide of bifeprunox (compound 3) is purified by crystallization from 700 ml acetonitrile and 100 ml water and recrystallization from 200 ml isopropanol. M.p.: 178-181° C. Using $^1$H-NMR spectroscopy, the purity of Compound 3 was determined to be greater than 96%.

Example 4

Formulations Used in Animal Studies

For oral (p.o.) administration: to the desired quantity (0.5-5 mg) of the solid test compound in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7. Remaining particles in the suspension were further suspended by using an ultrasonic bath.

For intravenous (i.v.) administration: compounds were dissolved in physiological saline (0.9% NaCl) and the pH was adjusted to 7.

For intraperitoneal (i.p.) administration: to the desired quantity (0.5-15 mg) of the solid test compound in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 5

Pharmacological Test Results

From the in vitro data (see table 1, below) it is evident that the N-oxide of SLV308 is much less active than the parent compound. It is also clear that the measured activity of N-oxide is real, and not caused by e.g. possibility that N-oxide was 'polluted' by small quantity of SLV308. This can be concluded from the observations that the potency ratios are not constant: their affinities for dopamine-$D_4$ receptors differ by a factor 10, whilst for dopamine-$D_2$ receptor affinity this ratio is a factor 100 or more.

The $ED_{50}$ of SLV308 as antagonist of apomorphine induced climbing behaviour is 0.07 mg/kg i.v. Under the same test conditions the $ED_{50}$ of the N-oxide is more than ten times higher: 0.90 mg/kg. However, when tested orally, both compounds, SLV308 and its N-oxide, were shown to be equipotent ($ED_{50}$-values of 0.75 and 0.79 mg/kg respectively). From these data it is evident that after oral dosing the SLV308 N-oxide is reduced to the corresponding tertiary amine: SLV308.

These findings were corroborated by measurements of plasma levels of SLV308 and its N-oxide after oral dosing with SLV308 and the N-oxide. After oral administration of SLV308 only trace amounts of the N-oxide were found in blood plasma, however, after oral administration of the N-oxide, plasma levels of the N-oxide and SLV308 were approximately equal.

TABLE 1 in vitro and in vivo pharmacology of SLV308 and its' N-oxide

| In vitro receptor affinity | | | SLV308 | N-oxide |
|---|---|---|---|---|
| receptor | $S^1$ | radioligand | $K_i$ (nM) | $K_i$ (nM) |
| Dopamine-$D_1$ | h | [$^3$H]-SCH 23390 | 160 | >1,000 |
| Dopamine-$D_2$ | h | [$^3$H]-spiperone | 10 | >1,000 |
| Dopamine-$D_{2S}$ | h | [$^3$H]-spiperone | 10 | >1,000 |
| Dopamine-$D_4$ | h | [$^3$H]-spiperone | 16 | 130 |
| Dopamine-$D_5$ | h | [$^3$H]-SCH 23390 | 250 | >1,000 |
| 5-$HT_{1A}$ | h | [$^3$H]-8-OH-DPAT | 3 | 200 |
| 5-$HT_{1B}$ | r | [$^3$H]-serotonin | 1,300 | >1,000 |
| 5-$HT_{1D}$ | b | [$^3$H]-serotonin | 400 | >1,000 |
| 5-$HT_{2A}$ | h | [$^3$H]-ketanserin | 1,600 | >1,000 |
| 5-$HT_{2C}$ | h | [$^{125}$I]-DOI | 800 | >1,000 |
| 5-$HT_3$ | r | [$^3$H]-GR 38032F | 3,200 | >1,000 |
| 5-$HT_7$ | h | [$^3$H]-LSD | 63 | >1,000 |
| $\alpha_1$-adrenergic | r | [$^3$H]-prazosin | 16 | >1,000 |
| $\alpha_{1A}$-adrenergic | r | [$^3$H]-prazosin | 32 | 630 |
| $\alpha_{1B}$-adrenergic | r | [$^3$H]-prazosin | 10 | 400 |
| $\alpha_2$-adrenergic | r | [$^3$H]-RX 821002 | 40 | 500 |
| $\alpha_{2C}$-adrenergic | h | [$^3$H]-MK912 | 63 | 400 |
| $\beta_1$-adrenergic | h | [$^3$H]-CGP 12177 | 320 | >1,000 |
| $\beta_2$-adrenergic | h | [$^3$H]-CGP 12177 | 1,000 | >1,000 |
| μ-opiate | r | [$^3$H]-DAMGO | 400 | >1,000 |
| κ-opiate | r | [$^3$H]-U 69593 | 1,000 | >1,000 |

| In vitro functional receptor activity | SLV308 | N-oxide |
|---|---|---|
| Human dopamine-$D_3$ receptor antagonism (p$A_2$) | 9.0 | <5.0 |
| Human dopamine-$D_3$ receptor agonism (p$EC_{50}$) | 8.9 | 7.3 |
| Human dopamine-$D_3$ receptor intrinsic activity (α) | 0.67 | 0.60 |

| In vivo pharmacology | SLV308 | N-oxide |
|---|---|---|
| Antagonism of apomorphine induced climbing behavior after intravenous dosing: $ED_{50}$ in mg/kg | 0.07 | 0.90 |
| Antagonism of apomorphine induced climbing behavior after oral dosing: $ED_{50}$ in mg/kg | 0.75 | 0.79 |
| Antagonism of 6-OH dopamine induced turning behavior after oral dosing: $ED_{50}$ in mg/kg | 0.032 | <1.0* |

$S^1$: (species): b = bovine, h = human, r = rat;
*to be quantified

The pharmacological data collected in the table above were obtained according to the protocols given above.

Example 6

Plasma Concentrations of Tertiary Amines and their N-Oxides

Bifeprunox, SLV308 and SLV318 as well as their respective N-oxides were individually administered (either intravenously (i.v.) or orally (p.o.)) to mice (3 animals per time point), after which their blood was analyzed by LC-MS (method see above) for both the parent amine and its N-oxide. Data were averaged (n=3), and collected in the tables below.

| | | Analyzed in blood | |
|---|---|---|---|
| administered | Time (hr) | Bifeprunox [ng/ml] | N-oxide [ng/ml] |
| Bifeprunox 0.5 mg/kg i.v. | 0 | 361 | 0 |
| | 0.17 | 334 | 57 |
| | 0.5 | 288 | 67 |
| | 1 | 175 | 35 |
| | 3 | 212 | 35 |
| | 7 | 69 | 11 |
| | 24 | 4 | 0 |
| N-oxide 0.5 mg/kg i.v. | 0 | 0 | 170 |
| | 0.17 | 133 | 134 |
| | 0.5 | 176 | 85 |
| | 1 | 134 | 33 |
| | 3 | 80 | 10 |
| | 7 | 33 | 5 |
| | 24 | 1.6 | 0 |

| | -continued | | |
|---|---|---|---|
| | 0.5 | 50 | 14 |
| | 1 | 17 | 3 |
| | 3 | 3 | 0 |
| | 7 | 0 | 0 |
| | 24 | 0 | 0 |
| SLV318 5mg/kg p.o. | 0 | — | — |
| | 0.17 | 71 | 0 |
| | 0.5 | 33 | 0 |
| | 1 | 19 | 0 |
| | 3 | 9 | 0 |
| | 7 | 2 | 0 |
| | 24 | 0 | 0 |
| N-oxide 5 mg/kg p.o. | 0 | — | — |
| | 0.17 | 1 | 1 |
| | 0.5 | 7 | 1 |
| | 1 | 20 | 2 |
| | 3 | 30 | 0 |
| | 7 | 7 | 0 |
| | 24 | 0 | 0 |

Conclusion: When administered to mice (either i.v. or p.o.), SLV318 is not metabolized to its N-oxide. When the N-oxide is administered intravenously, it is rapidly reduced to the parent compound: already after 10 minutes the concentration of SLV318 is higher than that of the N-oxide. When the N-oxide is administered orally, within ten minutes the concentration thereof in the plasma is equal to that of the parent molecule. Evidently, after oral dosing the N-oxide is a prodrug of SLV318. After 1 hour plasma concentrations of SLV318 do not significantly differ after dosing with either 5 mg/kg SLV318 p.o. or the same dose of its N-oxide.

The invention claimed is:

1. A compound of formula (1), which has a purity of greater than 96%, or a tautomer, a stereoisomer, or a pharmacologically acceptable salt thereof:

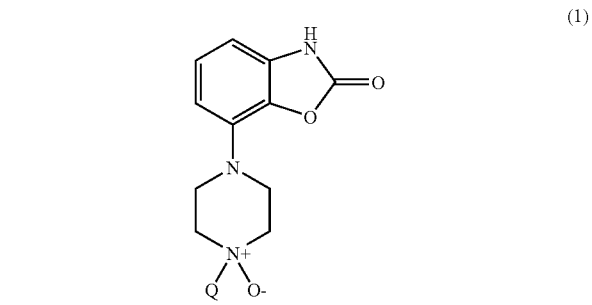

wherein:

Q is chosen from methyl, benzyl, and (1,1'-biphenyl)-3-yl-methyl.

2. The compound according to claim 1, wherein Q is methyl, and the compound is represented by formula (2):

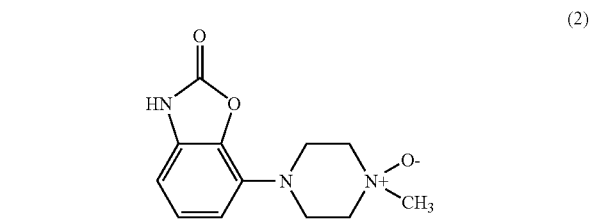

or a pharmacologically acceptable salt thereof.

3. The compound according to claim 1, wherein Q is benzyl, and the compound is represented by formula (3):

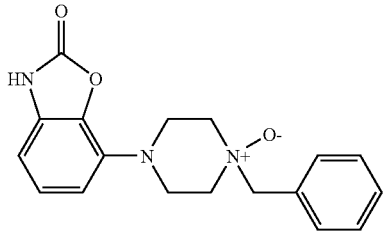

or a pharmacologically acceptable salt thereof.

4. The compound according to claim 1, wherein Q is (1,1'-biphenyl)-3-yl-methyl, and the compound is represented by formula (4):

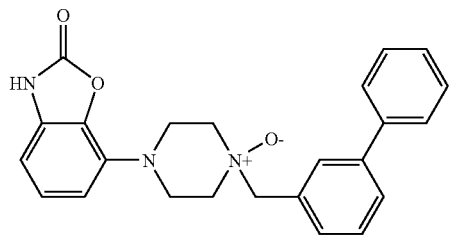

or a pharmacologically acceptable salt thereof.

5. A pharmaceutical composition comprising at least one pharmaceutically acceptable carrier and/or at least one pharmaceutically acceptable auxiliary substance, and a pharmacologically active amount of at least one compound of formula (1), a tautomer, a stereoisomer, or a pharmacologically acceptable salt thereof, or a mixture of at least two or more of the foregoing, as an active ingredient, wherein the compound of formula (1) has the structure:

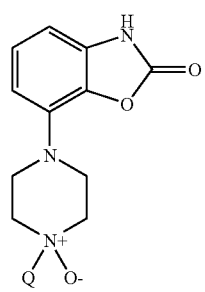

wherein:
Q is chosen from methyl, benzyl, and (1,1'-biphenyl)-3-yl-methyl.

6. A method for preparing a pharmaceutical composition comprising combining at least one compound of formula (1), a tautomer, a stereoisomer, or a pharmacologically acceptable salt thereof, or a mixture of at least two or more of the foregoing with at least one pharmaceutically acceptable carrier, at least one pharmaceutically acceptable auxiliary substance, or a combination thereof, wherein the compound of formula (1) has the structure:

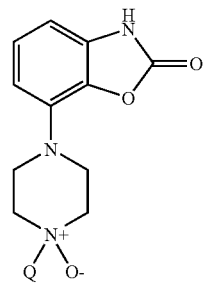

wherein:
Q is chosen from methyl, benzyl, and (1,1'-biphenyl)-3-yl-methyl.

7. A method for treating at least one CNS disorder chosen from anxiety depression, and Parkinson's disease, the method comprising:
administering a pharmacologically effective amount of at least one compound of formula (1), and a tautomer, a stereoisomer, or a pharmacologically acceptable salt thereof, or a mixture of two or more of the foregoing, to a patient in need thereof, wherein the compound of formula (1) has the structure:

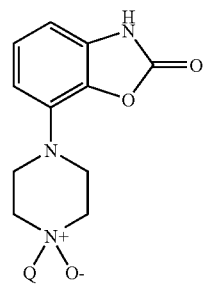

wherein:
Q is chosen from methyl, benzyl, and (1,1'-biphenyl)-3-yl-methyl.

8. A process for the preparation of a compound of formula (1), comprising:
oxidizing a compound of formula (1*) with hydrogen peroxide to yield a compound of formula (1), or a tautomer, a stereoisomer, or a pharmacologically acceptable salt thereof:

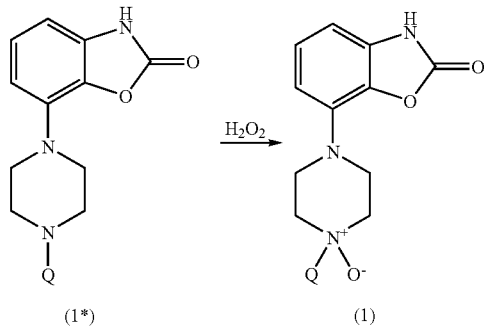

wherein:
Q is chosen from methyl, benzyl, or (1,1'-biphenyl)-3-yl-methyl.

* * * * *